United States Patent [19]

Paradies

[11] Patent Number: 5,254,728

[45] Date of Patent: Oct. 19, 1993

[54] COMPLEXES CONTAINING S(+)-PHENYL ALKANOIC ACIDS AND α-HYDROXYALKANOIC

[75] Inventor: Henrich H. Paradies, Iserlohn, Fed. Rep. of Germany

[73] Assignee: Medice Chem.-pharm. Fabrik Pütter GmbH & Co. KG, Iserlohn/Westfalen, Fed. Rep. of Germany

[21] Appl. No.: 792,485

[22] Filed: Nov. 15, 1991

[30] Foreign Application Priority Data

Nov. 15, 1990 [DE] Fed. Rep. of Germany ....... 4036459

[51] Int. Cl.⁵ .................. C07C 57/30; C07C 59/64; C07C 229/26; A61K 31/205

[52] U.S. Cl. .................. 562/496; 562/460; 562/465; 562/466; 562/490

[58] Field of Search ............... 562/496; 560/460, 465, 560/466, 490; 514/532, 533

[56] References Cited

U.S. PATENT DOCUMENTS 4,937,254 6/1990 Sheffield ........................ 514/420

Primary Examiner—Paul J. Killos
Attorney, Agent, or Firm—Townsend and Townsend Khourie and Crew

[57] ABSTRACT

Complexes containing S(+)-ibuprofen, method for the production of these complexes and pharmaceutical preparations containing these complexes are described.

22 Claims, No Drawings

COMPLEXES CONTAINING S(+)-PHENYL ALKANOIC ACIDS AND α-HYDROXYALKANOIC

The present invention relates to hydrogen-bridge-bound complexes having a stoichiometry of 1:1 of S(+)-phenyl alkanoic acids.

Compounds of S(+)-phenyl alkanoic acids and α-hydroxyalkanoic acids are already known. They are, however, not the specific complexes according to the invention but salts. As prior art in this respect attention is drawn to EP 0 424 028 A2, DE 39 22 441 A1, DE 25 08 895 C2, DE-AS 24 19 317, CH-PS 624 086, DE 38 14 887 C1 and DE38 36 863 A1.

Specification as laid open to inspection DE 38 36 863 A1 (1990) describes γ-butyrolactone which can readily dissolve water-insoluble non-steroidal antirheumatic agents, including (R, S)-ibuprofen. As solutions, preparations which are miscible with water and other liquids and can also be deleted as desired are named. The γ-butyrolactone is opened in the organism into the 4-hyroxybutyric acid and metabolized to $CO_2$ and water. In example 1, a pharmaceutical formulation in the form of a cream, ointment or gel is disclosed and contains inter alia 1 ml lactic acid. The addition of R, S or D, L-lactic acid is specified in a non-stoichiometric ratio (molar basis) in the (R, S)-ibuprofen formulation.

One problem underlying the present invention is the preparation of new substances on the basis of S(+)-phenyl alkanoic acids and α-hydroxyalkanoic acids and developing their advantageous use in pharmaceutical preparations.

This problem is solved according to the invention by hydrogen-bridge-bound complexes having a stoichiometry of 1:1 comprising S(+)-phenyl alkanoic acids and α-hydroxyalkanoic acids in which the complex bond is based on carboxylatecarboxyl interactions with a proton switch of the form $R_1$—COOH ... $^-$OOC—$R_2 \rightleftarrows$ $R_1$—COO$^-$ ... HOOC—$R_2$ where $R_1$—COOH denotes the S(+)-phenylalkanoic acids and $R_2$—COOH the α-hydroxyalkanoic acids and the pKa values relating, to the carboxyl group of the S(+)-phenyl alkanoic acids lie in the range of 3.5–3.9 and the pKa values relating to the carboxyl group of the in the α-hydroxyalkanoic acids lie in the range of 1.8–2.9.

Preferably, the α-hydroxyalkanoic acids have the following general formula:

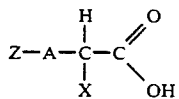

where
X = OH
Z = H. OH, $NH_2$
A = a bond or an alkylene chain which contains 1–10 carbon atoms and if required an amino group of 1–6 hydroxyl groups.

Preferably the pKa values relating to the carboxyl group of the α-hydroxyalkanoic acids lie in the range of 1.9–2.5.

Preferably, the complexes contain the enantiomers of lactic acid.

Preferably, as S(+)-phenyl alkanoic acids herein S(+)-ibuprofen or S(+)-naproxen shall be understood and are used. Preferably as S(+)-phenyl alkanoic acids herein the substances as detailed below shall be understood and are used. These substances comprise the following structure:

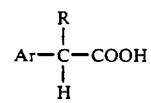

in which R is lower alkyl, Ar is preferably a monocyclic, polycyclic or ortho-condensed polycyclic aromatic group having up to twelve carbons in the aromatic system, e.g. phenyl, diphenyl, and naphthyl. The substituents of these aromatic groups comprise one or more halogen atoms, $C_1$–$C_4$ alkyls, benzyl, hydroxy, $C_1$–$C_2$ alkoxy, phenoxy and benzoyl groups. Examples of such substituted aryls are: 4-isobutyl-phenyl, 3-phenoxy-phenyl, 2-fluoro-4-diphenyl, 4'-fluoro-4-diphenyl, 6-methoxy-2-naphthyl, 5-chloro-6-methoxy-2-naphthyl and 5-bromo-6-methoxy-naphthyl, 4-chlorophenyl, 4-difluoro-methoxyphenyl, 6-hydroxy-2-naphthyl, and 5-bromo-6-hydroxy-2-naphthyl.

Preferably, the complexes consist of S(+)-phenyl alkanoic acids, preferably of S(+)-ibuprofen and α-hydroxyalkanoic acids.

According to the invention, the complexes of the invention are prepared by the following method steps:

a) for the preparation from aqueous medium (only water) or weakly buffered aqueous solutions covering a pH range between pH 5.5–7.5 (20° C.) a buffered aqueous solution, for example a 0.01M–0.001M-$K_2PO_4$/$KH_2PO_4$ buffer pH 6.0–7.5 (20° C.) is prepared and into it an equivalent amount S(+)-phenyl alkanoic acid is introduced with constant stirring;

b) the solution is heated with constant stirring to 40° C. (water bath) until a clear transparent solution is obtained (normally after 20 minutes) and all the S(+)-phenyl alkane acid has gone into solution;

c) thereafter the pH of the solution is adjusted to pH 5.5–6.0 by addition of diluted phosphoric acid ($H_2PO_4$) (20° C.) and then the equivalent (corresponding) amount of the α-hydroxyalkanoic acid is introduced with constant stirring;

d) the complex formation is terminated after 20 minutes, whereupon after cooling to 0°–4° C. the complexes precipitate in crystalline form and can be separated from the mother liquor via a sintered glass funnel or glass filter (1G4);

e) alternatively to method step d) the clear solution can be reduced in a rotary evaporator (water bath temperature 25°–30° C.) in the water jet vacuum to half the volume, whereupon a colourless (amorphous) deposit forms which is filtered off via a 1G4 glass filter and can be recrystallized from water/ethanol (70/30 V/V) or from ethyl acetate (100%).

The substances according to the invention are not a salt formation between an acidic group (carboxyl group of the ibuprofen) and a basic radical of the α-hydroxyalkanoic acid, but, as X-ray structure analysis and FT-IR spectra show, involve carboxylate-carboxyl interactions, the two carboxyl radicals of the α-hydroxyalkanoic acid and for example of the ibuprofen sharing a proton. This means that the complex is formed in accordance with the X-ray structure analysis by a hydrogen bridge without any participation of a basic group being observed.

The complexes according to the invention may be used advantageously in pharmaceutical preparations containing one or more complexes and possibly optionally additionally physiologically compatible usual extenders or carriers.

Particularly advantageous is a pharmaceutical preparation on the basis of phenyl alkanoic acids with anti-inflammatory, antipyretic, antimicrobial and analgesic effect, containing an active substance complex of a phenyl alkanoic acid and an α-hydroxyalkanoic acid and possibly additionally usual physiologically compatible auxiliary substances, in which the active substance complex consists of S(+)-phenyl alkanoic acids and α-hydroxyalkanoic acids.

Particularly advantageous is a pharmaceutical preparation on the basis of ibuprofen or naproxen with anti-inflammatory, antipyretic, antimicrobial and analgesic effect, containing an active substance complex of an ibuprofen or naproxen and α-hydroxyalkanoic acids and possibly additionally usual physiologically compatible auxiliary substances, in which the active substance complex consists of S(+)-ibuprofen or S(+)-naproxen and a α-hydroxyalkanoic acid and represents an amount by weight of 0.1-90% (w/w) of the composition.

Particularly advantageous is a pharmaceutical composition which contains 50 to 800 mg, preferably 100 to 600, in particular 100 to 300 mg S(+)-ibuprofen or S(+)-naproxen.

Particularly advantageous is a pharmaceutical preparation in which the suitable dose for oral and parenteral administration is in the range of 50 to 1200 mg daily, normally between 100 and 800 mg daily, preferably between 200 and 600 mg S(+)-ibuprofen daily and that the suitable doses for a topical administration of the complex lies in the range of 10-200 mg daily.

Hereinafter the "pharmaceutically active compound" in the broader sense is denoted as a complex. In medical use said pharmaceutically active compound may be administered orally, rectally, parenterally or topically, in particular however orally or topically. Thus, the therapeutical composition of the present invention may be any pharmaceutical preparation known per se for oral, rectal, parenteral or topical administrations. Pharmaceutically usual carriers which can be used in such pharmaceutical compositions are frequently described in pharmacy. The composition of this invention may correspond to 0.1-90% (w/w) of the active compound. The compositions represent normal unitary dosage forms. These dosage forms contain 50-800 mg, preferably 100-600 mg or 100-300 mg, S(+)-ibuprofen.

Oral administration forms according to this invention are preferred, such as tablets, capsules, syrup and aqueous or oily suspensions. Tablets may for example be prepared by mixing the active compound with inert extenders such as for example calcium phosphate in the presence of a disintegrating agent, for example starch, or lubricant, for example magnesium stearate, with subsequent conversion to tablet form in the normal production sense. The tablets may be prepared in the form of a retard formulation of the active compound by known methods. If desired, such tablets may be prepared by correspondingly known methods so that they do not disintegrate in the stomach, for example with the aid of cellulose, acetate, phthalate. Correspondingly, capsules may be made, for example soft or hard gelatin capsules, which contain the pharmaceutically active compound alone or in the presence of added auxiliary agents. These capsules may be made by conventional pharmaceutical technology, with or without stomachresistant coating. Other compositions for oral administration include aqueous solutions containing the active pharmaceutical compound in the presence of a nontoxic suspension agent, for example carboxymethyl cellulose and oily suspensions which contain the active pharmaceutical compound in the presence of a vegetable oil.

In accordance with this invention pharmaceutical formulations may be employed for topical administration of the active pharmaceutical compound. The pharmaceutically active compound in this case is dispersed in a pharmaceutically suitable cream, ointment or gel. A suitable cream can for example be prepared in that the active pharmaceutical compound is dispersed in a topical carrier, for example readily volatile paraffin in an aqueous medium with the aid of surfactants (detergents). An ointment can for example be prepared by mixing the pharmaceutically active compound with a topical carrier, for example mineral oil or paraffin or beeswax. A gel-like formulation can be prepared by mixing an active pharmaceutical compound with a topical carrier, for example Carbomer BP, in the presence of water. Topically administratable compositions may consist inter alia of a matrix which is able to disperse the active pharmaceutical compound in such a manner that the latter is administered transdermally by its close contact with the skin. A suitable transdermal composition may be prepared inter alia by mixing the pharmaceutically active compound with a topical carrier, as described above, together with a possible transdermal accelerator, for example dimethyl sulfoxide or propylene glycol.

Pharmaceutical formulations in accordance with this invention which are suitable for rectal administration are inter alia suppositories on the basis of polyethylene glycol or cocoa butter.

Pharmaceutical formulations for parenteral administration contain known pharmaceutical formulations, for example sterile suspensions or sterile solutions in a suitable solvent.

In some specific pharmaceutical formulations it appears expedient to have the pharmaceutical active compounds in the size of small particles, for example colloidal solutions or particulate suspensions of the order of magnitude of 0.1-1 μm (colloid mill).

If desired, in accordance with this invention compositions may also be prepared with other compatible pharmaceutical active substances.

These complexes according to the invention have anti-inflammatory, antipyretic and interesting antimicrobial properties as well as analgesic effects. These complexes have inter alia the advantage that after oral administration after a relatively short time they result in a substantially higher plasma level of S(+)-ibuprofen than S(+)-ibuprofen in the form of the free acid. These complexes are therefore particularly important in practice for treating acute pain; rapid onset with immediate freedom from pain can be achieved. The treatment of inflammations and pain is particularly important in rheumatic patients exhibiting indications such as primary chronic polyarthritis, arthridites of rheumatic origin, articular rheumatism and muscle rheumatism with their corresponding degrees of severity. These new complexes are particularly valuable for relieving pain, for example headache, dysmenorrhea, postoperative pain, postpartum pain and pain related to influenza and colds.

Accordingly, the invention describes in particular another aspect for treating pain or inflammatory fever after administering a therapeutically effective dose of said complex. Although the exact dose of the pharmaceutically active compound depends on a number of parameters, for example age of the patient, state of the patient, case history and compliance, a suitable dose both for oral and parenteral administrations of S(-)-ibuprofen complex is in the range of 50-1200 mg daily, normally between 100 and 800 mg daily, preferably between 200 and 600 mg S(+)-ibuprofen ibuprofen daily administered at one time or at several times.

With topical administration of this complex the corresponding dose lies in the range of 10-200 mg daily, generally being 20-100 mg daily, as ordered by the physician.

Advantageously, according to the invention the complexes of the invention may also be used in pharmaceutical preparations as are described in German application DE 40 15 794.6. Such isotropic solutions can be prepared by the following method steps:

a) heating of the carrier whilst stirring to above the melting point until an isotropic transparent liquid is present;

b) measuring the electrical conductivity and the viscosity at the temperature of the melting point to ensure the presence of an isotropic transparent liquid;

c) determination of the refractive index;

d) setting the desired concentration of the pharmaceutical active substances whilst observing the molar fraction, which at 37° C. must lie between 0.001 and 0.67;

e) introduction of the pharmaceutical active substance into the solvent with constant stirring;

f) stirring the mixture until the pharmaceutical active substance is dissolved and a transparent solution obtained;

g) measuring the differential refractive index increment $[(\Delta n/\Delta c)_{T/P=constant}]$ for determining the monomolecular solution and/or h) checking the native conformation and the monomolecularity of the pharmaceutical active substance in the solution by measuring the molar extinction coefficient in the UV range and taking the absorption spectrum and detection of the chiral configuration by measuring in the polarimeter and/or i) measuring the opacification to ensure a homogeneous solution and/or k) measuring the specific conductivity $[(\Omega)_{T,V=constant}]$ for controlling the ional concentration in the isotropic solution;

l) cooling the clear solution and preparing a galenic formulation;

m) further cooling of the solution to room temperature until the solution has solidified.

The invention will be explained in further detail hereinafter with reference to the example of the reactant lactic acid:

(R, S)-lactic acid is a liquid at room temperature (Fp: 16.8° C.) whilst the enantiomeric forms, D(−) and L(+)-lactic acid, are solid substances (Fp: 53°-54° C.). The enantiomers of lactic acid are slightly soluble in water, ethanol and ether and are not hydroscopic like D, L-lactic acid It has now been found that both D(−) and L(+)-lactic acid form with S(+)-ibuprofen a 1:1 molecular complex both in the solid state and in the liquid state (aqueous solution). The complex is formed by preparing an aqueous solution of D(−) or L(+)-lactic acid and heating it at 35° C. together with the corresponding stoichiometric amount, molar ratio 1:1 D(−) or L(+)-lactic acid and S(+)-ibuprofen, stirring and cooling again to 20° C. On further cooling to 0°-4° C. flake-like crystals appear which after filtration and drying at 20° C. under vacuum in a drying pistol have a melting point of 63°-65° C. The optimum rotation of these preparations is as follows:

$[\alpha]_{550}^{20}$ + 27° C. (=1.5, CHCl₃), for L(+)-lactic acid × S(+)-ibuprofen complex;

$[\alpha]_{550}^{20}$ + 2,5° C. (=2.5 in H₂O), for D(−)-lactic acid × S(+)-ibuprofen.

On recrystallization of the L(+)-lactic acid S(+)-ibuprofen complex from anhydrous ethanol other (polymorphous) crystalline forms result which according to powder patterns (Guinier method) also exhibit cell dimensions different to the crystals which can be obtained from aqueous or 50% (v/v) aqueous-ethanolic solutions. The latter crystalline forms (from aqueous-ethanolic solution) have a melting point of 58°-60° C. and in accordance with gravimetric and DSC measurements contain one molecule water as hydrate which is incorporated into the crystal lattice. Other polymorphous forms were obtained when crystallized from methanol/ethyl acetate 50% (v/v).

According to X-ray structure analytical investigations, in this case as well a hydrogen-bridge-bound complex is present between the carboxyl group of the S(-)-ibuprofen and the enantiomeric form of the lactic acid, in this case as well the carboxyl group. According to particulars in the literature and own conductimetric measurements the pKa of the lactic acid is 3.55-3.88 and that of the hydroxyl is pKa = 9.5, the lactic acid not being stable at this pH. This means that under the given production conditions and taking account of the pKa values of the S(+)-ibuprofen and the lactic acid, as with the α-amino acids as well, once again carboxyl-carboxylate hydrogen bridge bonds are involved which form this complex. However, further NMR and crystal-chemical investigations have shown that in addition, depending on the crystallization conditions, further hydrogen bridge bonds occur between all the hydroxyls of the lactic acid and the carboxyl groups of the S(+)-ibuprofen. In both cases, once again there is no salt-like or ion pair bond between S(+)-ibuprofen and the enantiomers of lactic acid. Crystalline compounds between S(+)-ibuprofen and the racemate of the lactic acid (D, L) were likewise obtained with stoichiometric reaction in alcoholic solution. These compounds consisting of S(+)-ibuprofen and (D, L)-lactic acid have a melting point of 28° C.; $[\alpha]_{550}^{20}$ = +51° (95%, EtOH), and exhibit the same structural principles as explained at the beginning for the pure enantiomers of the lactic acid.

The pharmacokinetic and pharmacodynamic behaviour, illustrated with reference to the example of the S(+)-ibuprofen × L(+)-lactic acid complex, follows that of complexes consisting of S(+)-ibuprofen and α-amino acids or amino sugars: Rapid effect onset with a $t_{max}$ of 20 minutes, a high AUC of 50 mg/ml x h compared with the free acid of only 40 mg/ml × h with a $t_{max}$ of 2 h, with the same active substance amount of 150 mg S(+)-ibuprofen. From these pharmacokinetic results it is apparent that the pharmaceutical preparation disclosed here is superior to the free acid of S(+)-ibuprofen.

EXAMPLES

1. Preparation of S(+)-ibuprofen-L-(+)-lactic acid complex 100 g L(+)-lactic acid are dissolved in 250 ml water whilst stirring at 20° C. (1.11 mol.) Under constant stirring 226.8 g (1.1 mol) S(+)-ibuprofen are introduced, the solution gradually being heated (within 10 minutes) to 35°–40° C. The pH of the solution should not exceed 6.0 when using a 0.001M NaHPO$_4$/NaH$_2$PO$_4$ buffer. With a simple aqueous solution (pH 5.5–6.0) it should be ensured that the pH does not drop below 4.0, this possibly making necessary a titration back to the original pH 5.5–6.0 again with diluted NaOH. The temperature of 35°–40° C. should be strictly observed to ensure that no segregation occurs. After about 30 minutes a clear solution is obtained which is cooled to 0°–4° C., whereupon the crystals of the complex form.

Alternatively, the clear solution can be cooled to 20° C. and concentrated to about 120 ml, whereupon a fine white deposit (amorphous) forms which can be filtered off via a 1G4 glass filter.

The material thus prepared is dried overnight under vacuum in a drying pistol at 20°–25° C. Yield: 85–90% of the theoretical value. Recrystallizing can be carried out from 50% (v/v) aqueous-ethanolic solution or ethanol/ethyl acetate (50/50 v/v). The material, recrystallized from pure organic solvent, or the dry powder has an Fp: 63°–65° C., $[\alpha]_{550}^{20}$ + 27° C. (=1.5, CHCl$_3$); crystals from aqueous-ethanolic solution (50% v/v) have an Fp: 58°–60° C. (decomposition) and $[\alpha]_{550}^{20}$ + 21° C. (c 1.5, CHCl$_3$).

2. Preparation of S(+)-ibuprofen-D-(−)-lactic acid complex

The procedure of example 1 is adopted. Melting point of the complex obtained from water or ethanol-ethyl acetate (50% v/v): Fp: 63° C.;
$[\alpha]_{550}^{20}$ + 2.5° C. (=2.5 in H$_2$O).

3. Preparation of S(+)-ibuprofen D, L-lactic acid complex 50 g (D, L)-lactic acid (0.55 mol) are dissolved in water (200 ml) whilst stirring at room temperature. Under constant stirring, 113.4 g S(+)-ibuprofen are added, the solution being brought to 30° C. within 10 minutes. After approximately half an hour complete dissolving occurs so that the reaction mixture can be cooled to 20° C. and prepared in accordance with the example. Yield: 90% of the theoretical value. Fp = 28° C.; $[\alpha]_{550}^{20}$ + 51° C. (95%, ethanol).

EXAMPLE 4

A pharmaceutical formulation can consist inter alia of

| | |
|---|---|
| S(+)-ibuprofen, L(+)-lactic acid | 215.5 mg |
| magnesium stearate, powder NF | 5.0 mg |
| poridoul USP | 20.0 mg |
| hydroxypropyl methyl cellulose USP 6 CPS | 4.0 mg |
| titanium dioxide USP | 1.5 mg |
| Tah USP, purified | 0.5 mg |
| hydroxypropyl cellulose LF, NFL 0.3% SiO$_2$ | 4.0 mg |

EXAMPLE 5

| | |
|---|---|
| S(+)-ibuprofen, L(+)-lactic acid | 307.0 mg |
| magnesium stearate, powder NF | 10.0 mg |
| hydroxypropyl methyl cellulose USP 6 CPS | 5.0 mg |
| Tah, USP | 1.0 mg |
| hydroxypropyl methyl cellulose LF, NFL 0.3% | 5.0 mg |
| Providone USP | 10.0 mg |
| titanium dioxide | 2.0 mg |

EXAMPLE 6

A pharmaceutical formulation for injection purposes can consist inter alia of:

| | |
|---|---|
| S(+)-ibuprofen, L(+)-lactic acid complex | 28.7 mg |
| Corresponding to 20.0 mg S(+)-ibuprofen | |
| Mannite | 20.0 mg |
| Water for injection purposes made up to | 1.0 ml |

EXAMPLE 7

The complexes consisting of S(+)-ibuprofen and L(+) or D(−)-lactic acid in the molar ratio 1:1 can also be prepared from salts of the enantiomers of the lactic acid.

In accordance with the following teaching, these complexes can be obtained almost quantitatively and with high optimum purity.

100 g L(−)-lithium lactate (1.04 mol) are dissolved whilst stirring at 20° C. in a mixture of 100 ml ethanol (96% p.a.) and 100 ml water (deionized). Under constant stirring, 214.5 g (1.04 mol) S(+)-ibuprofen are slowly added, ensuring that the pH value of the reaction mixture does not rise above pH 5.5, making the addition of 0.01N HCl necessary. The solution is heated to 30° C. for one hour, thereafter mixed with ethyl acetate (150 ml), the lithium salt precipitating and the complex being in the ester phase, and thereafter concentrated. The further procedure follows example 1.

I claim:

1. A hydrogen-bridge-bound complex having a stoichiometry or 1:1 comprising an S(+)-phenyl alkanoic acid and an α-hydroxyalkanoic acid in which the complex bond is based on a carboxylate-carboxyl interaction with a proton switch of the form R$_1$—COOH . . . $^{31}$OOC—R$_2$ ⇌ R$_1$—COO$^-$. . . HOOC—R$_2$ where R$_1$—COOH denotes the S(+)-phenyl alkanoic acid and R$_2$—COOH the α-hydroxyalkanoic acid and the pKa value relating to the carboxyl group of the S(+)-phenyl alkanoic acid lies in the range of 3.5–3.9 and the pKa value relating to the carboxyl group of the α-hydroxyalkanoic acid lies in the range of 1.8–2.9.

2. A complex according to claim 1, in which said α-hydroxyalkanoic acid has the following general formula:

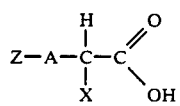

where
X = OH
Z = H, OH, NH$_2$
A = a bond or a member selected from the group consisting of an alkylene chain which contains 1–10 carbon atoms and alkylene chains substituted with a member selected from the group consisting of an amino group and 1-6 hydroxyl groups.

3. A complex according to claims 1 or 2, in which the pKa value relating to the carboxyl group of the α-hydroxyalkanoic acid lies in the range of 1.9-2.5.

4. A complex according to claims 1 or 2, in which said α-hydroxyalkanoic acid is an enantiomer of lactic acid.

5. A complex according to claim 1 or 2, in which said S(+)-phenyl alkanoic acid is a member selected from the group consisting of S(+)-ibuprofen or S(+)-naproxen are used.

6. A complex according to claims 1 or 2, in which said S(+)-phenyl alkanoic acid is S(+)-ibuprofen and said α-hydroxyalkanoic acid is in the D-form.

7. Pharmaceutical preparation containing one or more complexes to claim 1 and a physiologically compatible extender or carrier.

8. Pharmaceutical preparation according to claim 7 in which said α-hydroxyalkanoic acid is a basic α-hydroxyalkanoic acid.

9. Pharmaceutical preparation according to claim 7 or 8 in which said S(+)-phenyl alkanoic acid is a member selected from the group consisting of S(+)-ibuprofen and S(+)-naproxen, and said complex represents an amount by weight of 0.1 to 90% (w/w) of said preparation.

10. A complex according to claim s 7 or 8, characterized in that the S(+) phenyl alkanoic acid has a structure of the form

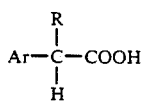

in which R is lower alkyl, Ar is a member selected from the group consisting of monocyclic, polycyclic and ortho-condensed polycyclic aromatic groups having up to twelve carbons in the aromatic system, and substituted derivatives of said aromatic groups bearing substituents selected from the group consisting of halogen atoms, $C_1$-$C_4$-alkyls, benzyl, hydroxy, $C_1$-$C_2$ alkoxy, phenoxy and benzoyl groups.

11. A complex according to claim 10, in which Ar is a member selected from the group consisting of 4-isobutyl-phenyl, 3-phenoxy-phenyl, 2-fluoro-4-diphenyl, 4'-fluoro-4-diphenyl, 6-methoxy-2-naphthyl, 5-chloro-6-methoxy-2-naphthyl, 5-bromo-6-methoxy-naphthyl, 4-chlorophenyl, 4-difluoro-methoxy-phenyl, 6-hydroxy-2-naphthyl and 5-bromo-6-hydroxy-2-naphthyl.

12. A method for the preparation of a complex of an S(+)-phenyl alkanoic acid and an α-hydroxyalkanoic acid, said method comprising:
 (a) combining said S(+)-phenyl alkanoic acid with an aqueous buffer solution having a pH range of 5.5 to 7.5 at 20° C.;
 (b) heating the combined acid and buffer solution of step (a) to 40° C. with constant stirring until a clear transparent solution is obtained and all of said S(+)-phenyl alkanoic acid is dissolved;
 (c) adjusting the pH of the solution resulting from step (b) to 5.5-6.0 by the addition of diluted phosphoric acid, then adding said α-hydroxyalkanoic acid in an equimolar amount relative to said S(+)-phenyl alkanoic acid to form a reaction mixture; and
 (d) after complex formation is complete, cooling said reaction mixture to precipitate therefrom said complex in crystalline form, and recovering said precipitated complex from said reaction mixture.

13. A method for the preparation of a complex of an S(+)-phenyl alkanoic acid and an α-hydroxyalkanoic acid, said method comprising:
 (a) combining said S(+)-phenyl alkanoic acid with an aqueous buffer solution having a pH range of 5.5 to 7.5 at 20° C.;
 (b) heating the combined acid and buffer solution of step (a) to 40° C. with constant stirring until a clear transparent solution is obtained and all of said S(+)-phenyl alkanoic acid is dissolved;
 (c) adjusting the pH of the solution resulting from step (b) to 5.5-6.0 by the addition of diluted phosphoric acid, then adding said α-hydroxyalkanoic acid in an equimolar amount relative to said S(+)-phenyl alkanoic acid to form a reaction mixture; and
 (d) after complex formation is complete, evaporating solvent from said reaction mixture to leave an amorphous solid, and recovering said solid.

14. A pharmaceutical preparation according to claim 7, in which said S(+)-phenyl alkanoic acid is a member selected from the group consisting of S(+)-ibuprofen and S(+)-naproxen, and said pharmaceutical preparation contains from 50 to 800 mg of said S(+)-phenyl alkanoic acid.

15. A pharmaceutical preparation according to claim 7, in which said S(+)-phenyl alkanoic acid is a member selected from the group consisting of S(+)-ibuprofen and S(+)-naproxen, and said pharmaceutical preparation contains from 100 to 600 mg of said S(+)-phenyl alkanoic acid.

16. A pharmaceutical preparation according to claim 7, in which said S(+)-phenyl alkanoic acid is a member selected from the group consisting of S(+)-ibuprofen and S(+)-naproxen, and said pharmaceutical preparation contains from 100 to 300 mg of said S(+)-phenyl alkanoic acid.

17. A pharmaceutical preparation according to claim 7 in the form of an isotropic solution in which:
 (a) said one or more complexes are dissolved in said carrier in a form which is a member selected from the group consisting of monomolecular and ionic forms;
 (b) said one or more complexes is in a conformation which is a member selected from the group consisting of native and enantiomeric conformations;
 (c) the molar fraction of said one or more complexes relative to said pharmaceutical preparation is from 0.001 to 0.67;
 (d) said carrier is molten, phase-uniform and isotropic at body temperature;
 (e) said isotropic solution solidifies at room temperature;
 (f) said isotropic solution when solidified is crystalline or noncrystalline, and contains said one or more complexes in crystalline form or in a form which can be crystallized out of said solidified isotropic solution;
 (g) said isotropic solution has an osmotic pressure and effects a molar freezing point reduction; and (h) said one or more complexes has a temperature-dependent diffusion coefficient and a temperature-dependent specific conductivity.

18. A method for achieving an anti-inflammatory, antipyretic, antimicrobial or analgesic effect in a subject, said method comprising treating said subject with a therapeutically effective amount of a complex according to claim 7.

19. A method in accordance with claim 18 comprising orally or parentally administering said complex to said subject at a dosage of 50 to 1200 mg daily.

20. A method in accordance with claim 18 comprising orally or parentally administering said complex to said subject at a dosage of 100 to 800 mg daily.

21. A method in accordance with claim 18 in which said S(+)-phenyl alkanoic acid is S(+)-ibuprofen, and said method comprises orally or parentally administering said complex to said subject at a dosage of 200 to 600 mg daily.

22. A method in accordance with claim 18 comprising topically administering said complex to said subject at a dosage of 10 to 200 mg daily.

* * * * *